United States Patent [19]

Sides

[11] Patent Number: 5,052,805
[45] Date of Patent: Oct. 1, 1991

[54] VENTILATION UNIT FOR A FLAME PHOTOMETRIC DETECTION DEVICE

[75] Inventor: Gary D. Sides, Alabaster, Ala.

[73] Assignee: CMS Research Corporation, Birmingham, Ala.

[21] Appl. No.: 581,532

[22] Filed: Sep. 12, 1990

[51] Int. Cl.$^5$ .................. G01J 3/443; G01N 21/72
[52] U.S. Cl. ..................... 356/315; 356/417
[58] Field of Search ................ 356/315, 417

[56] References Cited

U.S. PATENT DOCUMENTS

| 3,137,759 | 6/1964 | Isreeli | 356/315 |
| 3,791,743 | 2/1974 | Cody et al. | 356/417 |

FOREIGN PATENT DOCUMENTS

| 811082 | 3/1981 | U.S.S.R. | 356/315 |
| 1128625 | 9/1968 | United Kingdom | 356/417 |

OTHER PUBLICATIONS

Bulletin 4-7006, The N.I.L. Digital Flame Photometer, National Instrument Laboratories, Inc., May 1968.

Primary Examiner—F. L. Evans
Attorney, Agent, or Firm—Jennings, Carter, Thompson & Veal

[57] ABSTRACT

A ventilation unit for a flame photometric detector that utilizes a vent tube, which communicate with the combustion chamber of the detection device and a cap which fits onto the tube to form a tortuous light path, such that the escape of combustion products through the vent tube does not allow extraneous light to enter the combustion chamber, a series of threads and tabs on the tube and cap allow the cap to be threaded onto yet to fit loosely about the tube.

19 Claims, 2 Drawing Sheets

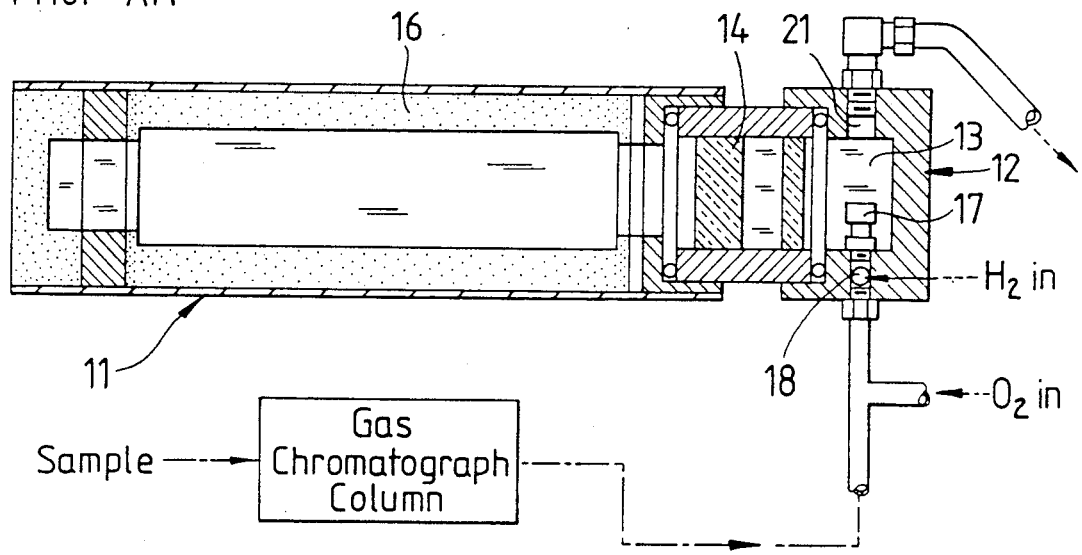
FIG. 1
Prior Art
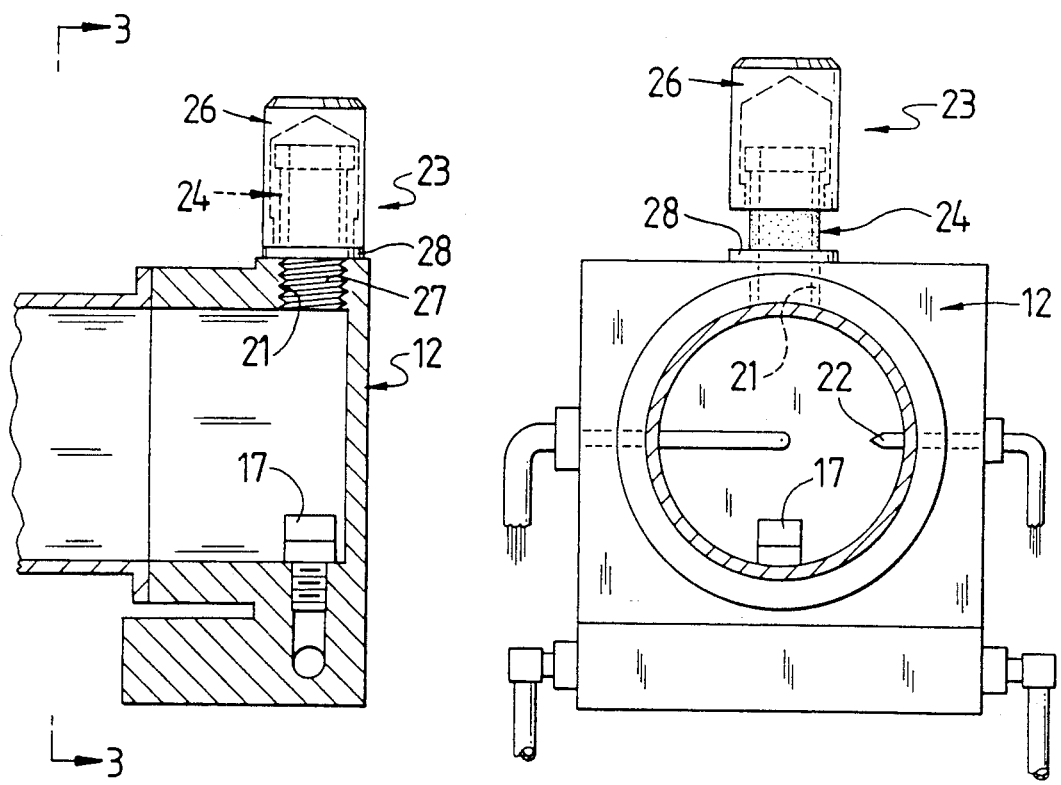
FIG. 2
FIG. 3

VENTILATION UNIT FOR A FLAME PHOTOMETRIC DETECTION DEVICE

FIELD OF THE INVENTION

This invention relates generally to the field of flame photometric detection devices. More specifically my apparatus relates to preventing ambient light from entering the ventilation aperture and interfering with the detection of light at preselected wavelengths while allowing sufficient ventilation of discharged gases and combustion products.

BACKGROUND OF THE INVENTION

The flame photometric detector has a significant commercial importance because of its simultaneous sensitivity and specificity for the determination of phosphorous and sulfur. In particular the flame photometer is used in combination with gas chromatographs or the continuous monitoring systems (as disclosed by U. S. Pat. No. 4,805,441) for the trace analysis of these phosphorous and/or sulfur containing compounds. In some instances the detection device may be capable of determining such compounds at concentrations as low as 10 parts per trillion. The flame detection of phosphorous and sulfur is based on the principal that, when a hydrocarbon having phosphorous or sulfur, is combusted in a hydrogen-rich flame, a chemiluminescent species is produced. These chemiluminescent species emit light at wavelengths (394-526 nm) characteristic for each element when the proper portion of the flame is viewed. The flame is fueled by $H_2$ that is piped directly into the burner at a rate of approximately 140 ML/min. In addition nitrogen carrier gas that transfers sulfur and/or phosphorous containing compounds from the GC column, is mixed with air and flows into the burner whereby the total air flow rate is 120 ML/min. As the gases and compounds of a sample are burned in the flame, exhaust from combustion is vented through a ventilation aperture above the flame.

With this ventilation opening the detection device is exposed to ambient light that may interfere with detection of the radiation emission of the burning sample. Devices known in the prior art have attempted to solve the problem by attaching an elbow tube within the vent and an elongated bent tubing is attached thereto so the tubing extends laterally of the detection device flame, and then downward. The tubing requires ambient light to make two diffractions to enter the chamber. This apparatus however still permits light to enter the flame chamber which may cause interference. In analysis of trace amounts as low as 10 parts per trillion it is imperative that any extraneous radiation be substantially impeded to avoid interference with detection of the sample radiation emission. Moreover, the lateral extension of the pipe permits it to remain cool during operation of the instrument causing condensation on tubing as the hot exhaust is discharged from the detector. This condensation drips on laboratory tables or wherever the instrument and device is placed. In addition, the condensation may further reflect light in the tubing allowing the light to enter the flame chamber.

SUMMARY OF THE INVENTION

It is the principal object of the present invention to provide a device that is vertically mounted within the ventilation aperture of a flame photometric detection device that substantially prevents radiation of ambient light from interfering with detection of radiation at selected wavelengths while providing sufficient ventilation of the flame chamber of the photometric detection device.

Yet another object of the present invention is to provide a device that does not allow condensation within the device.

These and other objects and advantages of my invention are accomplished through the use of a vent tube vertically mounted within the ventilation aperture of a flame photometric detection device, and a cap slidably secured over the tube such that surrounding light is substantially impeded from entering the detection device, and ventilation of the detection device is permitted. In addition, the size and vertical alignments allow the device to remain sufficiently heated to prevent any condensation therein.

BRIEF DESCRIPTION OF THE DRAWINGS

Apparatus embodying features of my invention are depicted in the attached drawings which form a portion of this disclosure and wherein:

FIG. 1 is a sectional view of a flame photometer detector and the prior art;

FIG. 2 is a sectional view of the detector with my apparatus attached;

FIG. 3 is a sectional view of the detector along line 3—3 of FIG. 2;

DESCRIPTION OF THE PREFERRED EMBODIMENT

Figure 4:
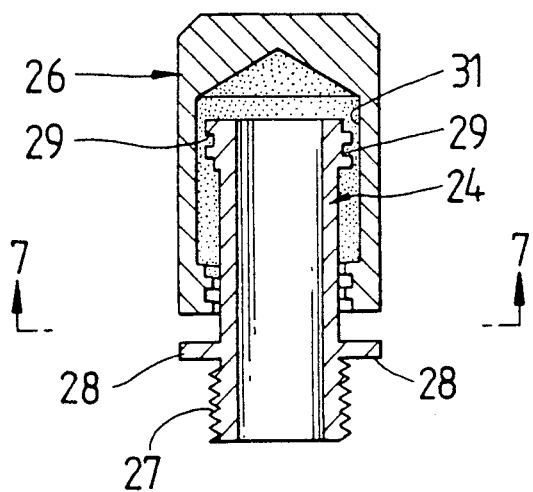
FIG. 4 is a sectional view of my vent cap.

It may be appreciated that my invention may be utilized with the design of the flame photometric detector (FPD) shown in FIGS. 1-3, that is used in combination with conventional gas chromatographs and continuous monitoring systems. The FPD 11 uses an aluminum block 12 having a cavity therein forming the flame chamber 13. An optical filter 14 is mounted adjacent the flame chamber 13 and has a bandpass of 394 or 526 nm for selectivity of sulfur and/or phosphorous containing compounds. A photomultiplier tube 16 is mounted behind the optical filter 14 for detection of radiant energy emitted by the incinerated phosphorous and/or sulfur containing compounds.

A burner 17 is mounted within the bottom of the flame chamber. The flame in the burner is fueled by $H_2$ that is piped directly to the burner via a plumbing line 18. Compounds separated in the GC column 19 are transferred to the burner by carrier gas nitrogen which is mixed with air or oxygen, via lines before reaching the burner. A ventilation aperture 21 is aligned with the burner in the top of the flame chamber 13, and allows for proper ventilation in the discharge of burned gases and other combustion products. The ignition of the gases at the burner is facilitated by a nichrome wire glow plug 22 suspended in the chamber 13 which is turned on when gases are flowing into the chamber. As compounds are transferred to the burner via the GC column, they are incinerated in the flame emitting light that is selectively transmitted to the photomultiplier, while the products of the combustion are blown through the ventilation aperture 21.

My ventilation unit 23 is vertically mounted within the ventilation aperture 21 as shown in FIG. 2. As illustrated in FIGS. 2-8 the device may include an aluminum tubular portion 24 vertically mounted within the aperture and a cap 26 slidably mounted thereon that inhibits light from entering the detection device while permitting sufficient ventilation of the products of combustion discharged axially from the tube 24. The mounting of the tube within the aperture may be facilitated by forming a standard external thread 27 adjacent the bottom of the tube and a matching internal standard thread within the aperture 21 so the tube may be bolted within the aperture. As both the tube 24 and block 12 are aluminum the fit is snug, substantially blocking ambient light from entering. In addition, a non-stick sealing tape sold under the trademark TEFLON tape may further be wrapped around the lower threaded portion 27 to further seal the junction between the tube 24 and block 12. In addition, the tube 24 need only be tall enough so that it remains heated during operation to prevent condensation thereon. A tube approximately one inch in height is sufficient.

Figure 5:
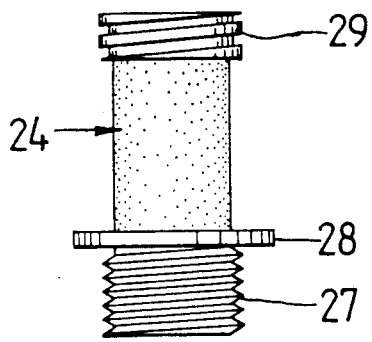
FIG. 5 is a side elevational view of my vent tube.

As further shown in FIGS. 4-5, the tube may have a flange portion 28 adjacent that portion of the tube mounted within the venting aperture 21 upon which the cap 26 rests. An upper flange having a channel extending therethrough forms a coarse thread 29 which serves to selectively retain the cap 26 on the tube 24. The thread 29 may be approximately 6 threads per inch and depends only far enough to retain the cap 26 on the tube 24. Intermediate the flange 28 and upper external thread 29 the tube is smooth and has a diameter slightly less than the maximum diameter of the upper thread 29 and the flange portion 28.

The cap 26 is an aluminum rod having a cylindrical cavity 31 therein that is cooperatively positioned over the tube to serve as a baffle means so gases discharged axially from the tube hit the top of the cavity and are dispersed laterally of the tube and then downward along the outer surface of the tube as shown in FIG. 4. A plurality of tabs 32 extend radially inward from the cavity surface 31 adjacent the opening of the cavity. These tabs 32 form an internal diameter of the opening that is approximately equal the maximum diameter of the upper threaded portion 29 on the tube 24 so the cap 26 may be screwed onto the tube and, secured thereon.

In addition, the internal diameter formed by the tabs 32 is greater than the diameter of the tube 2 defined by its smooth portion. Thus the cap 26 is axially slidable along the tube 24 intermediate the flange 28 and upper external thread 27.

Figure 7:
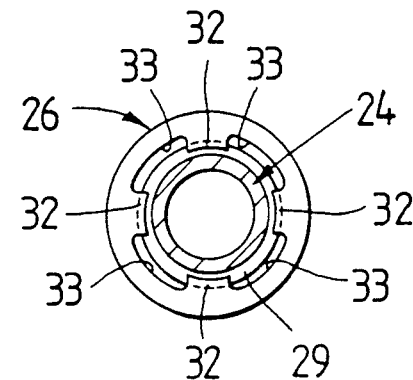
FIG. 7 is a sectional view taken along line 7—7 of FIG. 4 showing the bottom of my vent tube.
Figure 6:
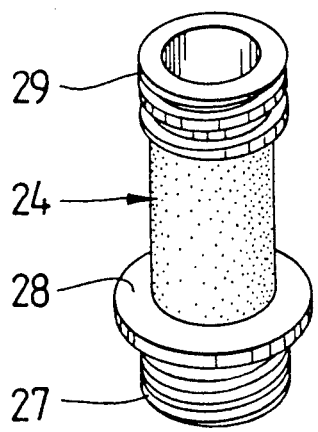
FIG. 6 is a perspective view of my vent tube.
Figure 8:
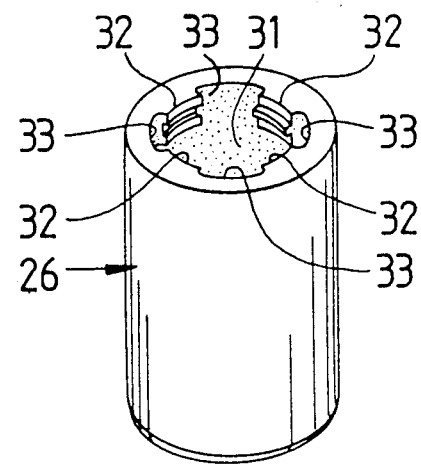
FIG. 8 is a bottom perspective view of my vent cap.

As further illustrated by FIG. 7 a plurality of recess 33 separate the radial tabs 32. The recesses 33 are integral with the surface of the cavity 31 and are spaced equidistantly about the circumference of the cavity. These recesses 33 aid in ventilation of the detection devices by allowing ventilation between the flange 28 and cap 26.

Note that cavity 3 is taller than the distance from the flange 28 to the top of tube 24 so that the top of the cavity is offset from the opening of the tube. Moreover the walls of the cavity are radially offset from the outer surface of the tube. Thus, gases discharged axially from the tube are displaced lateral of the tube opening. The burned gases then are directed by the walls of the cavity axially downwardly of the tube and cap through the recessed portions 33 in the opening of the cavity.

Note that the cooperative engagement of the tube and cap also create a tortuous path for ambient light to follow and enter the tube, substantially preventing any interference with detection of selected radiation in the detection device. Light entering between the cap 26 and flange 28 must survive a series of reflections off the outer surface of the tube 24 and the side of the cavity 31 and top of the cavity before entering the tube 24 and the flame chamber 13. In addition, the cavity surface 31 of the cap and outer surface of the tube 24, above the flange, may be painted black or anodized to reduce reflection of light and further inhibit ambient light from entering the detection device.

Cooperative engagement of the cap and tube also facilitates an easy ignition of the flame. As the hydrogen, carrier gas, and air are pumped into the burner and the flame chamber, the cooperative junction of the cap and tube allow the gases to build up within the tube so when the nichrome glow plug is turned on the gases are easily ignited. At the same time enough of the gases are discharged for a safe ignition. That is to say as the cap 26 is slidable on the tube, the explosive expansion of heated gas lifts the cap vertically along the tube 24 so pressure may be safely released upon ignition, while the cap 26 is retained by the upper threaded portion 29.

While I have shown my invention in one form, it will be obvious to those skilled in the art that it is not so limited but is susceptible of various changes and modifications without departing from the spirit thereof.

What I claim is:

1. A light blocking apparatus mountable to a ventilation opening of a flame photometric detection device such that combustion products discharged from the detection device are adequately ventilated comprising:
   (a) a tube vertically mounted within a ventilation opening of a flame photometric detection device; and
   (b) means slidably and selectively releasably secured atop said tube for impeding ambient light from entering the tube and the photometer while permitting sufficient ventilation of the detection device.

2. A light blocking apparatus as defined in claim 1 wherein said tube further comprises:
   (a) an outwardly extending upper flange depending from the top of said tube with said flange having a channel cut therein starting from the top of said upper flange and spiraling downward to the bottom of said flange forming an external thread; and
   (b) a smooth portion axially extending along a portion of the tube between said upper flange and said ventilation opening and having a diameter less than said flange.

3. Apparatus as defined in claim 1 wherein said impeding means further comprises a ventilation cap slidably secured on said tube having a cover portion extending over the top of the tube and a cylindrical portion depending from said cover portion and surrounding said tube with said cover offset from the tube and said cylindrical portion radially offset from the tube so exhaust discharged from the tube is ventilated.

4. A light blocking device as defined in claim 3 wherein said ventilation cap and said tube each have anodized surfaces to reduce reflection of any ambient light entering said light blocking device.

5. Apparatus as defined in claim 2 wherein said light impeding means further comprising:

(a) a baffle means slidably secured to said tube and cooperatively positioned over the tube to deflect and disperse combustion products axially discharged from the tube laterally thereof, said baffle means including a cylindrical portion open at a lower end and surrounding said tube and radially offset from said tube such that combustion products laterally dispersed by said baffle means are directed downwardly;

(b) a plurality of tabs extending radially inwardly from the lower end of said cylindrical portion for cooperative engagement with the channel of said upper flange means to releasably secure said light impeding means to said tube with said tabs forming an inner diameter at said lower end that is greater than the diameter of the smooth portion of said tube such that said light impeding means is vertically slidably mountable to said tube with said tabs defining;

a plurality of recesses there between permitting ventilation of exhaust of detection chamber.

6. Apparatus as defined in claim 3 wherein said ventilation cap further includes a blackened inner surface of said cylindrical portion to prevent reflection of any ambient light entering the cap.

7. Apparatus as defined in claim 3 wherein said tube further includes a blackened outer surface on said tube to prevent reflection of any ambient light entering the cap.

8. Apparatus as defined in claim 1 wherein said tube includes:
(a) an external threaded portion formed on the top of said tube for securing said light impeding means thereon;
(b) an outwardly extending lower flange adjacent that portion of the tube mounted within the flame photometric detection device; and
(c) a smooth portion axially extending along the tube between said threaded portion and said lower flange portions having a diameter less than both said threaded portion and said flange portion.

9. A device as defined in claim 8 wherein said impeding means comprises a ventilation cap slidably secured on said tube having a cover portion above the top of the tube and a cylindrical portion depending from said cover portion over said tube with said cover portion in spaced relation to said tube and said cylindrical portion radially offset from the tube and resting on said lower flange.

10. A device as defined in claim 8 wherein said light impeding means comprises:
(a) a baffle means cooperatively positioned above said tube such that said combustion products axially discharged from said tube are laterally dispersed;
(b) a cylinder depending from said baffle means over the tube to said lower flange, thereby holding said baffle means in spaced relation to the tube, and creating a tortuous path for ambient light to enter the detection device, and said cylinder being radially offset from the tube such that combustion products laterally dispersed by said baffle means are directed downwardly; and
(c) an internal threaded portion, adjacent the bottom of the cylinder, matching the upper threaded portion of said tube and resting on the lower flange, with said internal threaded portion forming an inner diameter of the cylinder greater than that of the smooth portion of the tube and having a plurality of recesses formed in and interrupting said internal threaded portion integral with the inner surface of the cylinder with said recesses spaced equidistantly about the circumference of the cylinder and permitting ventilation of combustion products axially along said tube.

11. A light blocking device as defined in claim 9 wherein said ventilation cap further includes a blackened inner surface to prevent reflection of any ambient light entering the cap.

12. A light blocking device as defined in claim 11 wherein said ventilation tube further includes a blackened outer surface on said ventilation tube to prevent reflection of any ambient light entering the cap.

13. A ventilation unit mounted within the ventilation opening of a flame photometric detection device that prevents ambient light from interfering with the detection of flame emissions of a sample incinerated in said photometric detection device comprising:
(a) a ventilation tube vertically mounted within a vent opening of a flame photometric detection device for directing combustion products from the detection chamber thereof;
(b) a baffle means slidably secured and cooperatively positioned on said tube such that said combustion products discharged axially of the tube are laterally dispersed thereof;
(c) means depending from said baffle means over the tube for directing said combustion products downward axially along the outer surface of said tube.

14. A ventilation unit as defined in claim 13 wherein said tube further includes:
(a) an upper external threaded portion depending from the top of said tube;
(b) a flange portion adjacent the portion of tube mounted within the vent, for engagement with the bottom of said directing means; and
(c) a smooth portion intermediate said flange and upper thread portions having a diameter slightly less than the maximum diameter of said upper threaded portion and said flange portion.

15. A ventilation unit as defined in claim 14 wherein said directing means further comprises:
(a) a cylinder depending from said baffle means and surrounding the tube and engaging said lower flange thereby holding said baffle means in spaced relation to the tube, and creating a tortuous path for ambient light to enter the detector, said cylinder being radially offset from the tube so combustion products laterally dispersed by said baffle means is directed downwardly axially along the outer surface of said tube; and
(b) an internal threaded portion adjacent the bottom of the cylinder matching the upper threaded portion of said tube so said cylinder may be secured thereon, said internal threaded portion forming an inner diameter of the cylinder greater than that of the smooth portion of the tube so said baffle means is slidably positioned axially above the tube and having a plurality of recesses interrupting said internal threaded portion integral with the internal surface of the cylinder with said recesses spaced equidistantly about the circumference of the cylinder.

16. A ventilation unit as defined in claim 15 wherein said cylinder further includes a blackened inner surface to prevent reflection of any ambient light entering the cylinder.

17. A ventilation unit as defined in claim 16 wherein said ventilation tube further includes a blackened outer surface on said ventilation tube to prevent reflection of any ambient light entering said cylinder.

18. A ventilation unit as defined in claim 14 wherein said baffle means, directing means and said tube each have anodize surfaces to reduce light reflection of any ambient light entering said ventilation unit.

19. A ventilation unit as defined in claim 13 wherein said tube further comprises:

(a) an outwardly extending upper flange depending from the top of said tube with said flange having a channel cut therein starting from the top of said flange and spiraling downward to the bottom of said flange to form a thread;
(b) an outwardly extending lower flange adjacent that portion of the tube mounted within the flame photometric detection device; and
(c) a smooth portion axially extending along the tube between said upper and lower flange.

* * * * *